(12) United States Patent
Blenk et al.

(10) Patent No.: US 10,036,816 B2
(45) Date of Patent: Jul. 31, 2018

(54) X-RAY DETECTOR WITH PROTECTIVE ELEMENT AND ADHESIVE ELEMENT

(71) Applicant: Siemens Healthcare GmbH, Erlangen (DE)

(72) Inventors: Caroline Blenk, Erlangen (DE); Thorsten Ergler, Erlangen (DE); Miguel Labayen De Inza, Forchheim (DE); Jan Wrege, Erlangen (DE)

(73) Assignee: Siemens Healthcare GMBH, Erlangen (DE)

( * ) Notice: Subject to any disclaimer, the term of this patent is extended or adjusted under 35 U.S.C. 154(b) by 0 days.

(21) Appl. No.: 15/479,756

(22) Filed: Apr. 5, 2017

(65) Prior Publication Data
US 2017/0293039 A1    Oct. 12, 2017

(30) Foreign Application Priority Data

Apr. 6, 2016   (DE) .................. 10 2016 205 702

(51) Int. Cl.
*G01T 1/24* (2006.01)
*A61B 6/00* (2006.01)
*A61B 6/03* (2006.01)

(52) U.S. Cl.
CPC .............. *G01T 1/244* (2013.01); *A61B 6/032* (2013.01); *A61B 6/4291* (2013.01); *G01T 1/242* (2013.01)

(58) Field of Classification Search
CPC .. A61B 6/032; A61B 6/03; G01T 1/20; G01T 7/00; G01T 1/2985; G01T 1/2928; G01T 1/24; G01T 1/242; G01T 1/244

USPC ....................................................... 250/370.14
See application file for complete search history.

(56) References Cited

U.S. PATENT DOCUMENTS

| 7,486,764 B2* | 2/2009 | Tkaczyk ................. G01T 1/249 250/370.09 |
| 7,696,483 B2 | 4/2010 | Tkaczyk et al. |
| 2002/0079458 A1* | 6/2002 | Zur ....................... G01T 1/2018 250/370.11 |
| 2004/0217294 A1* | 11/2004 | Zur ....................... G01T 1/2018 250/370.09 |
| 2005/0147813 A1 | 7/2005 | Gotz et al. |

(Continued)

FOREIGN PATENT DOCUMENTS

| DE | 10357321 A1 | 7/2005 |
| DE | 102013203894 A1 | 9/2014 |

(Continued)

OTHER PUBLICATIONS

German Office Action 102016205702.2 dated Dec. 6, 2016.

*Primary Examiner* — Taeho Jo
(74) *Attorney, Agent, or Firm* — Harness, Dickey & Pierce, P.L.C.

(57) ABSTRACT

An X-ray detector includes an anti-scatter grid, an electrode and a converter element for converting X-rays into electrical charges in a stacking arrangement. In an embodiment, the stacking arrangement is externally enclosed by a protective element. The protective element extends in the stacking direction such that an enclosed area is at least arranged between the anti-scatter grid and the converter element and along the entire height of the converter element in the stacking direction. An adhesive element is arranged between the anti-scatter grid and the electrode.

22 Claims, 4 Drawing Sheets

(56) References Cited

U.S. PATENT DOCUMENTS

| | | | | | |
|---|---|---|---|---|---|
| 2006/0110609 | A1* | 5/2006 | Eaton | .................... | C04B 41/009 428/446 |
| 2008/0175347 | A1* | 7/2008 | Tkaczyk | ................. | G01T 1/249 378/7 |
| 2009/0225938 | A1* | 9/2009 | Zeitler | ................. | G01T 1/1644 378/51 |
| 2011/0309250 | A1* | 12/2011 | Appleby | ............... | B23P 15/246 250/361 R |
| 2012/0148029 | A1* | 6/2012 | Kaneko | .................... | G21K 1/06 378/154 |
| 2012/0181437 | A1* | 7/2012 | Nelson | ................. | A61B 6/4216 250/366 |
| 2012/0256335 | A1* | 10/2012 | Shoji | ........................ | G01T 1/00 264/2.7 |
| 2012/0313056 | A1* | 12/2012 | Baran | ..................... | H01B 1/22 252/519.21 |
| 2014/0034838 | A1* | 2/2014 | Appleby | ............... | B23P 15/246 250/366 |
| 2015/0030120 | A1* | 1/2015 | Ergler | .................. | A61B 6/4233 378/19 |
| 2015/0060685 | A1* | 3/2015 | Maad | ..................... | G01T 1/185 250/385.1 |
| 2015/0085990 | A1* | 3/2015 | Virshup | ................. | G21K 1/025 378/154 |
| 2015/0092918 | A1* | 4/2015 | Crocco | ............ | H01L 27/14676 378/62 |
| 2015/0362603 | A1* | 12/2015 | Ellwood | ................. | G01T 1/243 250/370.08 |
| 2016/0102228 | A1* | 4/2016 | Thatcher | .................... | C09J 7/10 524/401 |

FOREIGN PATENT DOCUMENTS

| | | |
|---|---|---|
| DE | 102013226669 A1 | 6/2015 |
| DE | 102014211602 A1 | 12/2015 |

* cited by examiner

X-RAY DETECTOR WITH PROTECTIVE ELEMENT AND ADHESIVE ELEMENT

PRIORITY STATEMENT

The present application hereby claims priority under 35 U.S.C. § 119 to German patent application number DE 102016205702.2 filed Apr. 6, 2016, the entire contents of which are hereby incorporated herein by reference.

FIELD

At least one embodiment of the invention generally relates to an X-ray detector, a detector module and a medical device.

BACKGROUND

In X-ray imaging, for example in computer tomography, angiography or radiography, counting directly-converting X-ray detectors can be used. The X-rays or photons can be converted into electrical signal pulses. Besides the counting of events, counting X-ray detectors also enable information about the energy of the detected X-ray quanta to be obtained. New possibilities are thus opened up for the analysis and evaluation of signal pulses in medical imaging.

As converter material for the converter element or the sensor, for example CdTe, CZT, CdZnTeSe, CdTeSe, CdMnTe, InP, $TlBr_2$, $HgI_2$, GaAs or others can be used. The energy of the incident ionizing radiation is immediately converted into electrical charges, so-called electron-hole pairs. A voltage is applied to the converter element, for example for CdTe, CZT, CdZnTeSe, CdTeSe or CdMnTe in the range of −500 to −2000V, between an electrode as a cathode and another electrode as an anode to separate the charges of the electron-hole pairs triggered in the converter element. The cathode can be designed as continuous electrode. The anode can be designed as a pixelated electrode. The voltage or the high voltage is applied to the electrode by way of an external high-voltage source via an electrically conductive contact. X-ray quanta can trigger electron-hole pairs in the converter element by way of energy deposition. The electron-hole pairs are separated by the applied voltage and the charge carriers selected by the polarity of the voltage can be sucked or drifted to the anode. In this way, an electrical signal pulse can be triggered in the read-out and/or the analysis unit. As a rule, the converter element is joined to a read-out and/or an analysis unit flat in a stacking arrangement, for example an integrated circuit (Application Specific Integrated Circuit, ASIC), via solder connections, electrically conducting adhesive or other methods. The electrical signal pulses are evaluated by an analysis unit, for example an ASIC. The stacking arrangement having the converter element and the read-out- and/or analysis unit is connected to a further substrate, for example a circuit board, a ceramic substrate such as, for example, HTCC or LTCC or others. The electrical connections for read-out of the read-out and/or the analysis unit can be formed by way of vias (through silicon via, TSV) or wire bond.

An X-ray detector for image recording of an object irradiated by X-rays which has a number of detector modules arranged adjacently to one another in a longitudinal direction, in a stack formation comprising a sensor layer with a sensor surface, is known from DE 10 2013 226 669 A1, wherein in each case a high voltage can be applied to the sensor surfaces for the detection of X-rays, and wherein an insulation foil which covers the sensor layers on the facing stacking sides of adjacent detector modules transversely with respect to the longitudinal direction is arranged in a gap between two adjacent detector modules respectively.

A detector module for an X-ray detector comprising a sensor layer with a sensor surface in a stack formation, to which a high voltage can be applied for the detection of X-rays, and wherein a related protective foil is arranged on at least two side faces of the stack formation, is known from DE 10 2014 211 602 A1.

A high-tack adhesive mass, based on an adhesive mass containing at least polyisobutylene and at least one tackifying resin, is known from DE 10357321 A1, wherein the molecular weight distribution of the polyisobutylene has two relative maxima, namely one between 50000 and 200000 and a second between $1.0 \times 10^6$ and $3.5 \times 10^6$.

A photon counting detector which has a directly-converting material and a data collection system is known from U.S. Pat. No. 7,696,483 B2.

In the event of mechanical damage, for example if an X-ray detector or a detector module falls and/or is struck against a hard object, the converter element may break into small fragments, particles or dust which can then get into the environment. CdTe, CZT, CdZnTeSe, CdTeSe and CdMnTe are hazardous substances and detrimental to health and so even in the event of mechanical damage, no dust and/or larger particles should get into the environment. Either while handling during production or when replacing a module in a clinical setting, after mechanical damage no small fragments, particles or dust of the converter element should get into the environment. At present, there is still no solution for the problem of mechanical protection. X-ray detectors or detector modules are handled very carefully to avoid mechanical damage.

SUMMARY

Embodiments of the invention include an X-ray detector, a detector module and a medical device which enable protection of the environment from particles of the converter element in the event of mechanical damage.

An embodiment of the invention is directed to an X-ray detector; an embodiment of the invention is directed to a detector module; and an embodiment of the invention is directed to a medical device.

An embodiment of the invention relates to an X-ray detector having an anti-scatter grid, an electrode and a converter element for converting X-rays into electrical charges in a stacking arrangement. The stacking arrangement is externally enclosed by a protective element. The protective element extends in the stacking direction such that an enclosed area is at least arranged between the anti-scatter grid and the converter element and along the entire height of the converter element in the stacking direction. An adhesive element is arranged between the anti-scatter grid and the electrode.

Furthermore, an embodiment of the invention relates to a detector module having an anti-scatter grid, a plurality of electrodes and a plurality of converter elements for converting X-rays into electrical charges in a stacking arrangement. The stacking arrangement is externally surrounded by a protective element. The protective element extends in the stacking direction such that an enclosed area is embodied at least between the anti-scatter grid and the plurality of converter elements and along the entire height of the converter element in the stacking direction. An adhesive element is embodied between the anti-scatter grid and the plurality of electrodes.

Furthermore, an embodiment of the invention relates to a medical device having an X-ray detector according to an embodiment of the invention or a detector module according to an embodiment of the invention. Advantageously, the advantages of the X-ray detector according to an embodiment of the invention or the detector module according to an embodiment of the invention can be transferred to the medical device. Advantageously, pollution or contamination of the surroundings or environment can be avoided. Advantageously, regulations to protect the environment and users can be observed.

According to one embodiment of the invention, the medical device is a computed tomography system. Advantageously, the escape of particles or dust of the converter material from the X-ray detector or the detector module can be avoided. Advantageously, consistent image quality and dose utilization can be achieved by way of the space-saving protective element and the adhesive element.

BRIEF DESCRIPTION OF THE DRAWINGS

Example embodiments of the invention are explained in more detail hereinafter with reference to drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

An embodiment of the invention relates to an X-ray detector having an anti-scatter grid, an electrode and a converter element for converting X-rays into electrical charges in a stacking arrangement. The stacking arrangement is externally enclosed by a protective element. The protective element extends in the stacking direction such that an enclosed area is at least arranged between the anti-scatter grid and the converter element and along the entire height of the converter element in the stacking direction. An adhesive element is arranged between the anti-scatter grid and the electrode.

The stacking arrangement is executed in a stacking direction. The stacking direction can, for example, be aligned at least approximately in the direction of the X-rays emitted by a source of radiation. The anti-scatter grid is closest to the source of radiation. Looking from the direction of the source of radiation, the converter element is located behind the anti-scatter grid. Furthermore, the stacking arrangement may have a two-dimensional illumination unit between the electrode and the anti-scatter grid. The illumination unit can be designed to illuminate the converter element evenly with additional radiation, for example IR, UV or visible light.

The anti-scatter grid is designed to reduce the influence of the X-ray image by reducing the photons or X-rays scattered in the patient or object of investigation. The lattice walls of the anti-scatter grid can be aligned in the direction of the X-rays emitted by the source of radiation so that the anti-scatter grid is preferably permeable for X-rays falling directly from the source of radiation onto the X-ray detector.

The protective element may comprise part of the anti-scatter grid or a bracket of the anti-scatter grid. The anti-scatter grid can be bridge-like in construction so that the bridge pillars ensure distance from the converter element and are also designed to enable the anti-scatter grid to be connected via a fastening element between the bridge pillars and for example a module support or the read-out unit. The protective element can be a foil. The protective element may at least partially comprise a foil and at least partially a bracket of the anti-scatter grid. An adhesive tape can be used as a protective element. The protective element is designed such that it externally surrounds the stacking arrangement. The protective element is designed such that an enclosed area is at least arranged between the anti-scatter grid and the converter element and along the entire height of the converter element in the stacking direction. The enclosed area is a volume between the anti-scatter grid and the converter element which is limited laterally by the protective element. The anti-scatter grid has grid openings, wherein the restricted area can connect to the grid openings resulting in the possibility that the enclosed area is not airtight with regard to the exchange of air, gas or particles. The protective element can also be designed such that the enclosed area is airtight with regard to the exchange of air or particles. The protective element can, for example, cover the entire surface of the side of the anti-scatter grid averted from the rays. The anti-scatter grid can be completely sealed so that no particles and no dust can escape through the anti-scatter grid and at the same time the grid openings are permeable for X-rays.

The adhesive element can be arranged extensively, in particular across the entire surface, between the anti-scatter grid and the electrode. The entire surface of the side of the anti-scatter grid averted from the rays can be covered with the adhesive element. The entire surface of the side of the electrode averted from the rays can be covered with the adhesive element. The adhesive element can be an adhesive foil, a tack coat or an adhesive layer. The adhesive element is sticky or tacky. Tacky can mean that the particles or dust adhere firmly to surfaces after the application of brief, light pressure or after contact with the adhesive element. The adhesive element can be sticky or tacky permanently or over a prolonged period of time, for example years. The adhesive element can be resistant to X-rays.

An embodiment of the invention reduces or even prevents or minimizes the escape of particles after mechanical damage of the converter element. An embodiment of the invention includes furthermore encapsulating the interior of the X-ray detector or the detector module in which the converter element is located. The inventors have recognized that apertures above and below the converter element from which particles or dust of the converter element escape can be avoided or sealed to this end. The protective element or the lateral encapsulation can be at least partially formed of a special very thin tape or adhesive tape.

In the event of the mechanical destruction of the converter element, particles which initially remain in the encapsulation or the sealed area may arise. However, should the protective element or the foil acquire a crack or the like, particles can escape and contaminate the environment, for example during transport, further handling, shipping, etc.

The inventors have recognized that with the most extensive possible lining of the encapsulated interior or the enclosed area with a sticky substance, the particles adhere thereto and cannot escape. The adhesive element can be above the converter element or the electrode. The adhesive element can be on the anti-scatter grid, on the illumination unit or on the electrode. The adhesive element may have a sticky substance. The protective element may also have an adhesive surface which also serves as a particle-binding adhesive surface.

Furthermore, the protective element can serve as protection from contact. Without the protective element, the converter element would be exposed and could be touched by the service technician or a production assistant during handling. This can lead to, for example, fat deposits on the side of the converter element. The fat deposits can reduce the creepage distances, possibly resulting in a short circuit between the upper side of the converter element to which approximately −1 kV can be applied, and a 0V potential on the analysis unit or the read-out unit or the ceramic support.

Advantageously, contamination of the environment following mechanical damage to converter elements can be prevented or greatly reduced. Above and below the converter element, the escape of particles or dust can be countered through the skillful embodiment of the module support and the anti-scatter grid or the illumination unit, for example a bracket of the anti-scatter grid, as part of the protective element. In addition, a very thin adhesive foil can complete the protection unit laterally, forming an enclosed area. Advantageously, the protective element can serve as contact protection. Advantageously, contamination of the converter element, in particular at the edges, can be avoided. Advantageously, a short circuit can be avoided.

Advantageously, the protective element, in particular the foil, has an insulating property with respect to adjacent X-ray detectors or detector modules. Advantageously, in the event of the failure of an applied voltage on an X-ray detector or a detector module, flashovers between adjacent X-ray detectors or detector modules can be avoided. Advantageously, the air and creepage distances can be increased. Advantageously, the escape of particles or dust from the converter material can be avoided or reduced by the adhesive element following mechanical damage. Advantageously, the particles or the dust can adhere to a tack coat inside the enclosed area.

According to one embodiment of the invention, the adhesive element has an adhesive surface on the side facing the electrode. The electrode can be embodied on the converter element. If particles or dust arise as a result of mechanical damage, the particles or the dust can immediately adhere to the sticky surface facing the electrode. Advantageously, the distribution of the particles or the dust is countered by the physical proximity of the sticky surface to the converter element. In addition, the side of the adhesive element averted from the electrode may also have an adhesive surface, for example to enable adherence of the particles or dust on both sides of the adhesive element in the event of the destruction of the adhesive element.

According to one embodiment of the invention, the adhesive element has an adhesive, an adhesive composition, an acrylate, a silicone, a rubber or a rosin resin. The adhesive surface for the adherence of particles or dust should cover as extensive an area as possible. The adhesive element should be radiation-resistant and its adhesive action must not significantly deteriorate in the course of its lifetime of ~10 years. Advantageously, a permanent sticky or tacky surface can be provided for the adherence of particles or dust. Advantageously, the adhesive element can have a lasting effect in preventing the escape of particles or dust. The adhesive element can have double-sided adhesive tape which adheres permanently on one side and remains tacky on the other side. The adhesive element can alternatively have transfer adhesive tape, the tacky adhesive composition being applied directly to the material or substrate for adherence. The tacky adhesive mass can be a so-called adhesive. The adhesive element may have adhesives such as acrylates, rubbers or silicon which are applied on a substrate, frequently on a plastic material. In the case of roll material, a so-called liner can provide additional protection for the rolled adhesive surface.

A transfer adhesive tape can only consist of a liner and the adhesive composition. Sticky resins, for example rosin resin, can be added to high-tack adhesive mass for adhesive mixing to increase the tack. The adhesive element may have resins such as, for example, rosin, in poorly evaporating solvents. Poorly evaporating can mean that the solvent does not fully evaporate over a period of years under operating conditions. Low molecular, amorphous and non-polar rubber with high chain mobility can be used as a solvent, for example.

According to one embodiment of the invention, the adhesive element has a bonding agent which fulfills the Dahlquist criterion. Solid matter which fulfills the so-called Dahlquist criterion, i.e. which has a module smaller than 0.3 Mpa, displays adhesive behavior, also described as tackiness. Advantageously, an adhesive surface can be designed for adherence of the particles or the dust. Acrylates can have the least tackiness and best adherence. In the case of double-sided adhesive tape, these can be suitable for the permanently adhesive side. For silicone, the properties can be determined by the degree of cross-linking.

According to one embodiment of the invention, the adhesive element is arranged directly on the electrode. The electrode may have a continuous planar extension. The adhesive element can be arranged or embodied flat on the electrode. The electrode can be grid-like or netlike in design, wherein points of contact of the adhesive element and converter element can be provided in the grid or network apertures. Advantageously, the particles or the dust can adhere to the adhesive element in direct physical proximity.

According to one embodiment of the invention, the adhesive element is arranged directly on the anti-scatter grid. Advantageously, the particles or the dust can adhere to the adhesive element, wherein the particles or the dust can adhere over a greater area, for example if only a small area of the converter element is damaged. Advantageously, a further adhesive surface to which the particles or the dust can adhere can be embodied on the side walls or the protective element. Advantageously, the entire enclosed area can be coated with a sticky layer.

According to one embodiment of the invention, the protective element is electrically insulating. Advantageously, flashovers to adjacent X-ray detectors or detector modules can be avoided.

According to one embodiment of the invention, the protective element has a foil. The detector modules or X-ray detectors in a detection device can be arranged with a very narrow assembly gap to keep the non-radiation-sensitive area, the dead zone, as well as the pitch break, i.e. deviations from the regular pixel geometry between the detector modules or X-ray detectors along a detection device, as small as possible to satisfy image quality and dose requirements. Accordingly, a very thin foil can be used for the protective element.

Furthermore, the likewise very thin tack coat can have sufficient strength to be able to guarantee durability of at least 10 years for the climate conditions in accordance with an authorization. Advantageously, the protective element and any of its adhesives in the beam path of the X-rays from the source of radiation to the converter element is X-ray resistant.

According to one embodiment of the invention, the foil is in the range of 30 μm to 180 μm thick. Advantageously, the foil can fit into the assembly gap without compromise as a result of an enlarged dead zone or an enlarged pitch gap. The foil can preferably be approximately 80 μm thick, wherein it advantageously has sufficient protection from voltage flashovers.

According to one embodiment of the invention, the adhesive element is externally enclosed by the protective element. The adhesive element can connect the protective element without a gap. Advantageously, all the particles or the dust can adhere to the adhesive element. Advantageously, no particles or dust can get past between the adhesive element and the protective element.

According to one embodiment of the invention, the X-ray detector also has an analysis unit, a substrate and/or a module support. The analysis unit can be an ASIC (Application Specific Integrated Circuit). Advantageously, the signals can be directly evaluated in the X-ray detector. Advantageously, the X-ray detector may have increased mechanical stability. Advantageously, the X-ray detector may have a device on the substrate or the module support for fastening the anti-scatter grid.

According to one embodiment of the invention, the protective element extends in the stacking direction such that the protective element is arranged at least partially along the anti-scatter grid, the analysis unit, the substrate and/or the module support in the stacking direction. Advantageously, the protective element can enclose the X-ray detector over a larger area in the stacking direction so that particles or dust, including from other components of the stack formation, are not emitted to the environment, or to a reduced extent. Advantageously, damage to adjacent X-ray detectors or detector modules can be avoided.

Furthermore, an embodiment of the invention relates to a detector module having an anti-scatter grid, a plurality of electrodes and a plurality of converter elements for converting X-rays into electrical charges in a stacking arrangement. The stacking arrangement is externally surrounded by a protective element. The protective element extends in the stacking direction such that an enclosed area is embodied at least between the anti-scatter grid and the plurality of converter elements and along the entire height of the converter element in the stacking direction. An adhesive element is embodied between the anti-scatter grid and the plurality of electrodes.

The detection device may comprise a number of detector modules which can be assembled and dismantled individually to replace individual units when there are electrical faults. A detector module has a plurality of converter elements each with an electrode. The detector module may also have a number of analysis units. The detector module may also have a shared substrate or a number of substrates. The detector module may also have a shared module support. The protective element may surround the plurality of converter elements. A shared protective element can be provided on the detector module. A shared adhesive element can be provided in the detector module.

The assembly gap, for example between adjacent detector modules, can be 60 μm to 500 μm. The protective element can be embodied with the aid of a thin protective layer, for example a foil. The foil can be 30 μm to 180 μm thick. The foil can preferably be 80 μm thick. Advantageously, the foil can insulate the converter elements of the detector module from adjacent detector modules. Advantageously, the foil can protect the converter element from mechanical damage and from contamination. Advantageously, no particles or dust can escape from the enclosed area.

Furthermore, an embodiment of the invention relates to a medical device having an X-ray detector according to an embodiment of the invention or a detector module according to an embodiment of the invention. Advantageously, the advantages of the X-ray detector according to an embodiment of the invention or the detector module according to an embodiment of the invention can be transferred to the medical device. Advantageously, pollution or contamination of the surroundings or environment can be avoided. Advantageously, regulations to protect the environment and users can be observed.

According to one embodiment of the invention, the medical device is a computed tomography system. Advantageously, the escape of particles or dust of the converter material from the X-ray detector or the detector module can be avoided. Advantageously, consistent image quality and dose utilization can be achieved by way of the space-saving protective element and the adhesive element.

Figure 1:
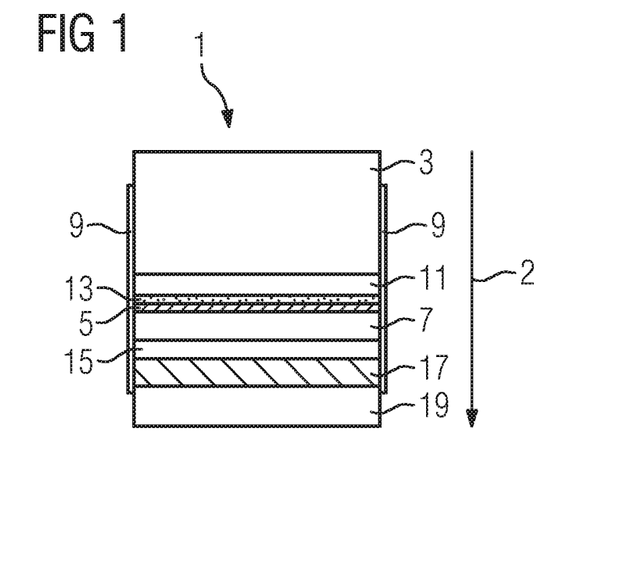
FIG. 1 shows a schematic view of a concept of an X-ray detector according to the invention in accordance with a first embodiment.

FIG. 1 shows an example embodiment of the X-ray detector 1 according to the invention in accordance with a first embodiment. The X-ray detector 1 has an anti-scatter grid 3, an electrode 5, a converter element 7 for converting X-rays into electrical charges, an analysis unit 15, a substrate 17 and a module support 19 in a stacking arrangement in the stacking direction 2. The stacking arrangement is externally surrounded by a protective element 9.

The protective element 9 extends in the stacking direction 2 such that an enclosed area 11 is at least arranged between the anti-scatter grid 3 and the converter element 7 and along the entire height of the converter element 7 in the stacking direction 2. The protective element 9 extends in the stacking direction 2, for example from a section of the anti-scatter grid 3 to a section of the module support 19.

An adhesive element 13 is arranged on the electrode 5 between the anti-scatter grid 3 and the electrode 5. The adhesive element 13 has an adhesive surface on the side facing the electrode 5. The adhesive element 13 has an adhesive, an adhesive composition, an acrylate, a silicone, a rubber or a rosin resin. The adhesive element 13 has a bonding agent which fulfills the Dahlquist criterion. Solids which fulfill the so-called Dahlquist criterion, i.e. which have a module smaller than 0.3 MPa, display adhesive behavior, also described as tackiness. The adhesive element 13 is arranged directly on the electrode 5. The adhesive element 13 is arranged or embodied flat on the electrode 5. The protective element 9 is electrically insulating. The protective element 9 has a foil. The foil is in the range of 30 μm to 180 μm thick, preferably approximately 80 μm. The adhesive element 13 finishes externally with the protective element 9.

Figure 2:
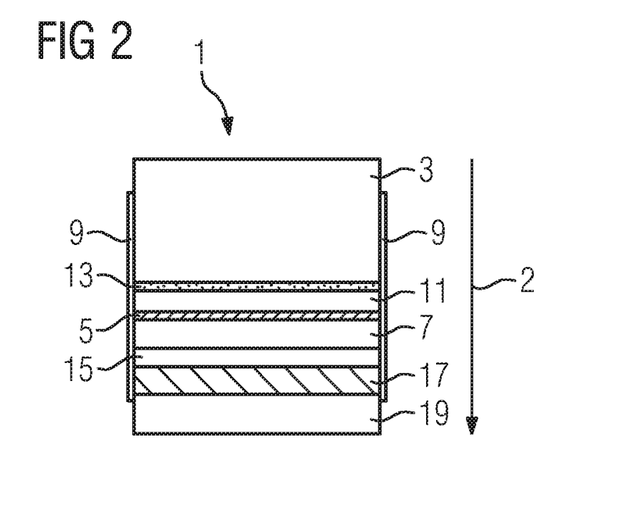
FIG. 2 shows a schematic view of a concept of an X-ray detector according to the invention in accordance with a second embodiment.

FIG. 2 shows an example embodiment of the X-ray detector 1 according to the invention in accordance with a second embodiment. An adhesive element 13 is arranged directly on the anti-scatter grid 3 between the anti-scatter grid 3 and the electrode 5.

Figure 3:
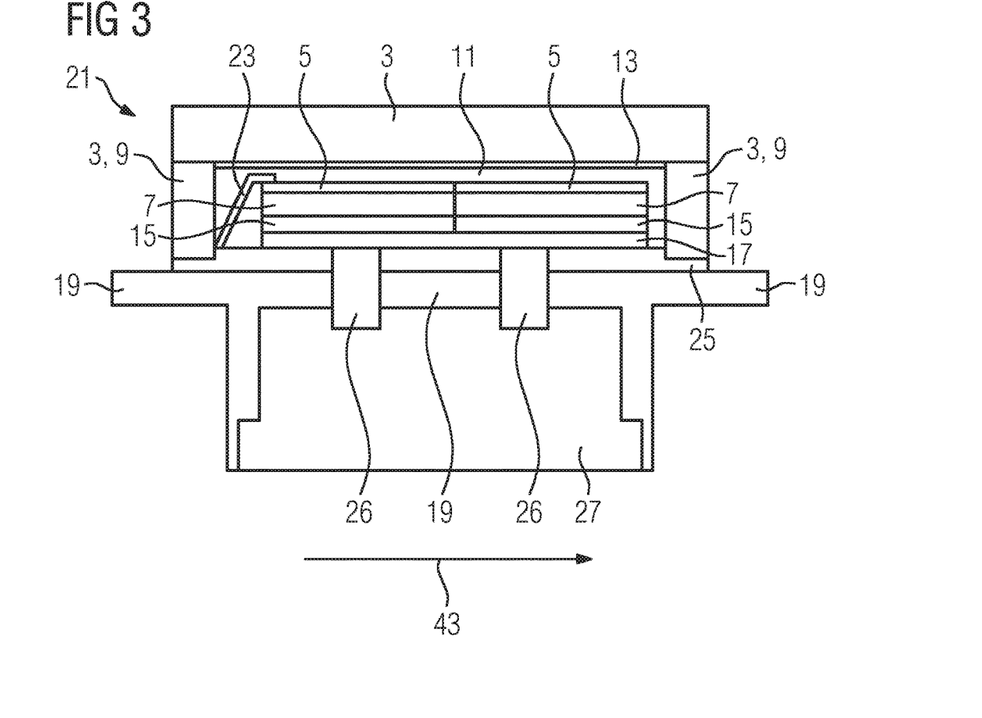
FIG. 3 shows a schematic view of a concept of a detector module according to the invention in accordance with a first embodiment.

FIG. 3 shows an example embodiment of the detector module 21 according to the invention in accordance with a first embodiment. The detector module 21 has an anti-scatter grid 3, a plurality of electrodes 5 and a plurality of converter elements 7 for converting X-rays into electrical charges, a plurality of analysis units 15, a substrate 17, a read-out unit 25 and a module support 19 in a stacking arrangement. The detector module 21 can have a divergent number of analysis units 15 and converter elements 7. The stacking arrangement is externally surrounded by a protective element 9.

The protective element 9 extends in the stacking direction such that an enclosed area 11 is embodied at least between the anti-scatter grid 3 and the plurality of converter elements 7 and along the entire height of the converter element 7 in the stacking direction. An adhesive element 13 is embodied between the anti-scatter grid 3 and the plurality of electrodes 5. For the sake of clarity, the protective element 9 was omitted in the plane of the figure, in other words, along the rotational axis 43. A voltage is applied to the electrode 5 via a voltage supply 23. The adhesive element 13 is arranged on the anti-scatter grid 3.

The protective element 3,9 is embodied in the figure on the right and left next to the stacking arrangement as part of the anti-scatter grid 3 or as a bracket of the anti-scatter grid 3. Furthermore, module electronics 27 which are connected to the read-out unit 25 via the data connection 26 are arranged on the module support 19. Furthermore, the module support 19 can have a fastening device for assembly in the detection device.

Figure 4:
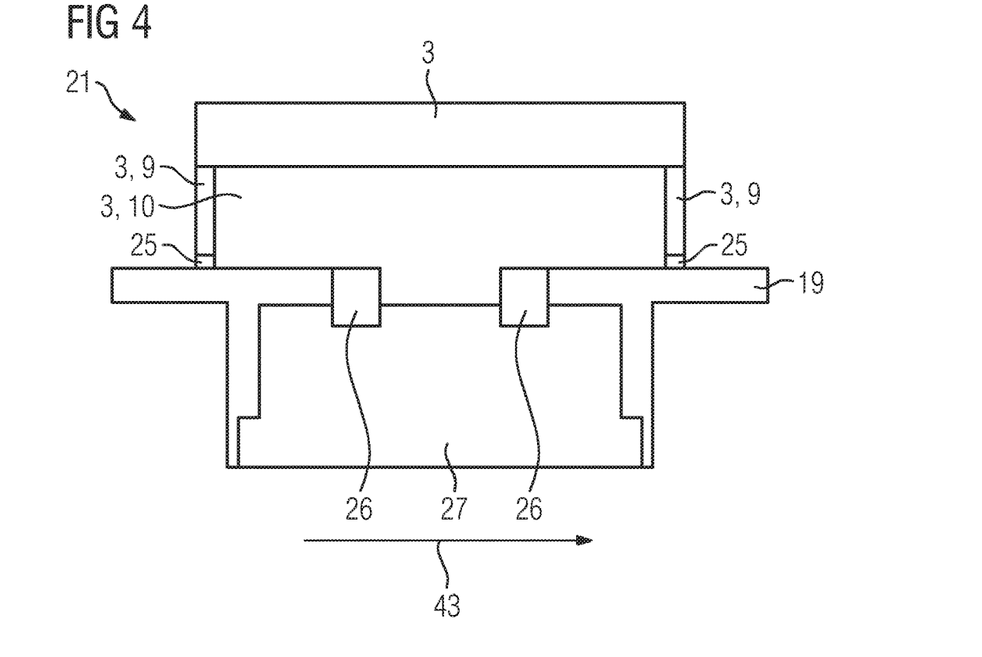
FIG. 4 shows a schematic view of a concept of a detector module according to the invention in accordance with a second embodiment.

FIG. 4 shows an example embodiment of the detector module 21 according to the invention in accordance with a second embodiment. Here the protective element 9 in the view from above is shown completely, in other words, also in the plane of the figure. The protective element 9 is externally arranged around the stacking arrangement. In the plane of the figure, in other words along the rotational axis 43, the protective element 9 is embodied as a foil 10. Perpendicular to the plane, in other words along the longitudinal axis, the protective element 9 is embodied as part of the anti-scatter grid 3. Jointly the protective element 9 is formed. The enclosed area is demarcated by the protective element 9.

Figure 5:
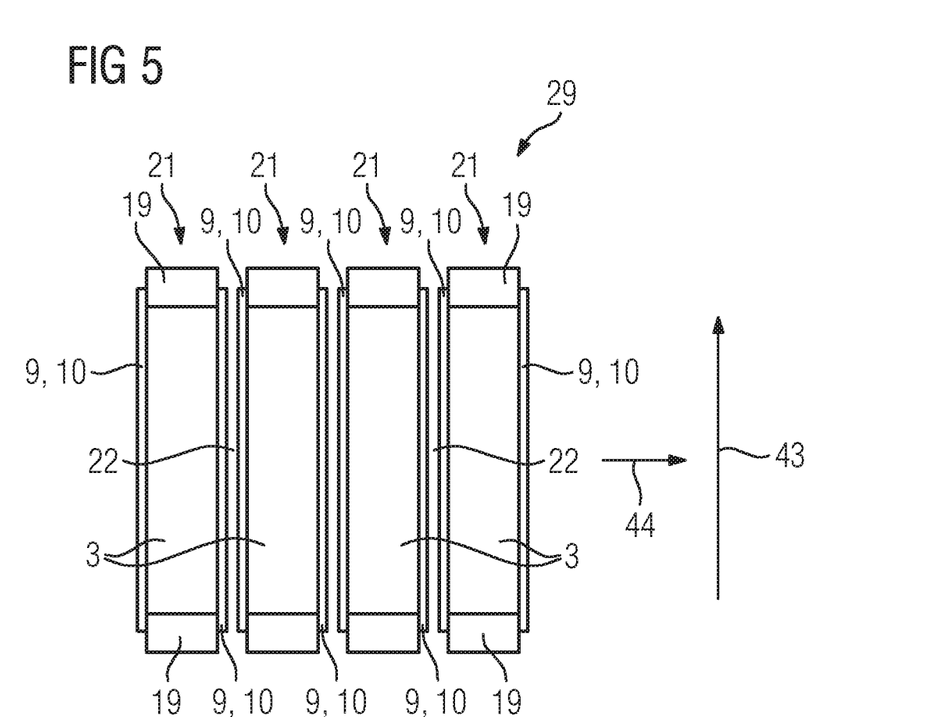
FIG. 5 shows a schematic view of a concept of a detection device with an arrangement of detector modules according to the invention.

FIG. 5 shows an example embodiment of a detection device 29 with an arrangement of detector modules 21 according to the invention. The detection device 29 is shown in a view from above from the source of radiation in relation to the anti-scatter grid 3. The detector modules 21 are arranged side by side along the longitudinal axis 44 of the detection device 29. The extension of the detector module 21 is greater in the direction of rotation 43 than in the longitudinal direction 44. A gap 22 or assembly gap is embodied between each of the detector modules 21. The foil 10 is arranged in the direction of rotation 43 on the outer sides of the detector modules 21 as part of the protective element 9. The detection device 29 can be curved in the longitudinal direction 44.

Figure 6:
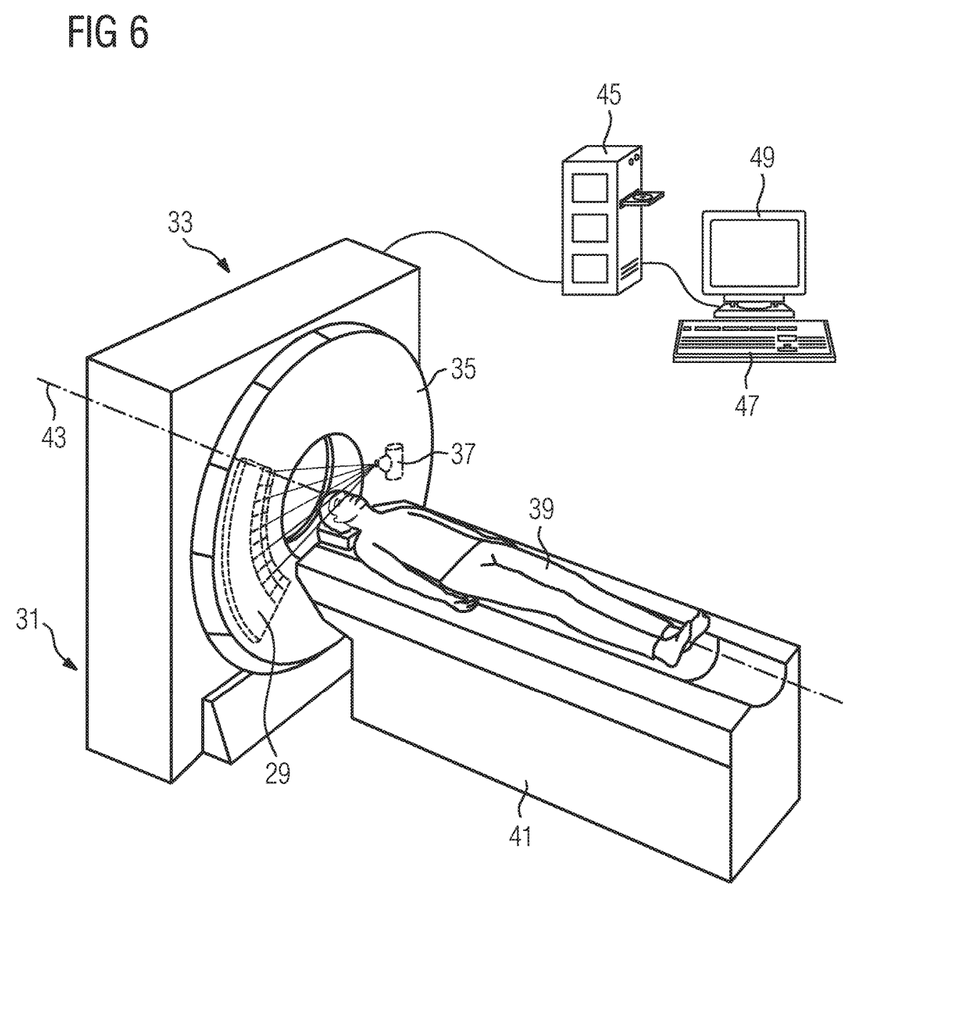
FIG. 6 shows a schematic view of a concept of a computed tomography system according to the invention.

FIG. 6 shows an example embodiment of the computed tomography system 31 with a detection device 29 according to the invention. The detection device 29 has the X-ray detector 1 and/or a number of detector modules 21 according to an embodiment of the invention. Preferably, the detector modules 21 have a plurality of converter elements in a two-dimensional matrix or arrangement, for example 1×3 converter elements along the rotational axis z 43. The computed tomography system 31 contains a gantry 33 with a rotor 35. The rotor 35 comprises an X-ray source 37 and the detection device 29 according to the invention. The patient 39 is supported on the patient couch 41 and can be moved along the rotational axis z 43 by the gantry 33. An arithmetic unit 45 is used to control and calculate the cross sections. An input device 47 and an output device 49 are connected to the arithmetic unit 45.

Although the invention was illustrated in more detail by the preferred example embodiment, the invention is not restricted by the disclosed examples and other variations can be derived therefrom by a person skilled in the art without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray detector, comprising:
   a stacking arrangement including at least
      an anti-scatter grid;
      an electrode; and
      a converter element configured to convert X-rays into electrical charges;
   at least one protective element externally surrounding at least side portions of the stacking arrangement and extending at least along an entire height of the converter element in a stacking direction, wherein an enclosed area is formed within the stacking arrangement, the enclosed area being a volume of space forming a gap which is at least arranged in between (i) the anti-scatter grid and (ii) the electrode and the converter element, and is limited laterally by the at least one protective element; and
   at least one adhesive element arranged on at least one of the anti-scatter grid and the electrode and enclosed externally by the at least one protective element, the at least one adhesive element including
      a first adhesive surface adhered to the at least one of the anti-scatter grid and the electrode, and
      a second adhesive surface exposed to the enclosed area so as to form an interior coating for adherence of particles or dust present within the enclosed area resulting from mechanical damage of the converter element.

2. The X-ray detector of claim 1, wherein the at least one adhesive element includes an adhesive, an adhesive composition, an acrylate, a silicone, a rubber or a rosin resin.

3. The X-ray detector of claim 1, wherein the at least one adhesive element includes a bonding agent which fulfills the Dahlquist criterion.

4. The X-ray detector of claim 1, wherein the first adhesive surface is adhered to the electrode and the second adhesive surface faces the anti-scatter grid.

5. The X-ray detector of claim 1, wherein the first adhesive surface is adhered to the anti-scatter grid and the second adhesive surface faces the electrode.

6. The X-ray detector of claim 1, wherein the at least one protective element is electrically insulating.

7. The X-ray detector of claim 1, wherein the at least one protective element includes a foil.

8. The X-ray detector of claim 7, wherein the foil is in a range of 30 μm to 180 μm.

9. The X-ray detector of claim 1, wherein the stacking arrangement further includes at least one of:
   an analysis unit;
   a substrate; and
   a module support.

10. The X-ray detector of claim 9, wherein the at least one protective element extends in the stacking direction such that the at least one protective element is arranged at least partially along at least one of the anti-scatter grid, the analysis unit, the substrate and the module support in the stacking direction.

11. A medical device comprising the X-ray detector of claim 1.

12. The medical device as claimed in claim 11, wherein the medical device is a computed tomography system.

13. The X-ray detector of claim 1, wherein the stacking arrangement further includes:
   an analysis unit;
   a substrate; and
   a module support.

14. The X-ray detector of claim 13, wherein the at least one protective element extends in the stacking direction such that the at least one protective element is arranged at least partially along at least one of the anti-scatter grid, the analysis unit, the substrate and the module support in the stacking direction.

15. The X-ray detector of claim 1, wherein the at least one adhesive element comprises:
   a first adhesive element arranged on the anti-scatter grid, wherein the first adhesive element includes a first adhesive surface adhered to the anti-scatter grid and a second adhesive surface facing the electrode, and
   a second adhesive element arranged on the electrode, wherein the second adhesive element includes a first adhesive surface adhered to the electrode and a second adhesive surface facing the anti-scatter grid.

16. The X-ray detector of claim 15, wherein the at least one protective element comprises a first protective element including a first interior adhesive surface and a second protective element including a second interior adhesive surface, at least a portion of each of the first interior adhesive surface and the second interior adhesive surface being exposed to the enclosed area so as to form the interior coating, such that the enclosed area is entirely surrounded by the interior coating for the adherence of particles or dust present within the enclosed area resulting from mechanical damage of the converter element.

17. The X-ray detector of claim 16, wherein the first interior adhesive surface of the first protective element is adhered to a first side portion of the stacking arrangement and the second interior adhesive surface of the second protective element is adhered to a second side portion of the stacking arrangement.

18. A detector module, comprising:
   a stacking arrangement including at least
      an anti-scatter grid;
      a plurality of electrodes; and
      a plurality of converter elements configured to convert X-rays into electrical charges;
   at least one protective element externally surrounding at least side portions of the stacking arrangement and extending at least along an entire height of the plurality of converter elements in a stacking direction, wherein an enclosed area is formed within the stacking arrangement, the enclosed area being a volume of space forming a gap which is at least formed in between (i) the anti-scatter grid and (ii) the plurality of electrodes and the plurality of converter elements, and is limited laterally by the at least one protective element; and
   at least one adhesive element formed on at least one of the anti-scatter grid and the plurality of electrodes and enclosed externally by the at least one protective element, the at least one adhesive element including
      a first adhesive surface adhered to the at least one of the anti-scatter grid and the plurality of electrodes, and
      a second adhesive surface exposed to the enclosed area so as to form an interior coating for adherence of particles or dust present within the enclosed area resulting from mechanical damage of one or more of the plurality of converter elements.

19. A medical device comprising the detector module of claim 18.

20. The medical device as claimed in claim 19, wherein the medical device is a computed tomography system.

21. The detector module of claim 18, wherein the at least one adhesive element comprises:
   a first adhesive element arranged on the anti-scatter grid, wherein the first adhesive element includes a first adhesive surface adhered to the anti-scatter grid and a second adhesive surface facing the plurality of electrodes, and
   a second adhesive element arranged on the plurality of electrodes, wherein the second adhesive element includes a first adhesive surface adhered to the plurality of electrodes and a second adhesive surface facing the anti-scatter grid.

22. The detector module of claim 21, wherein the at least one protective element comprises a first protective element including a first interior adhesive surface and a second protective element including a second interior adhesive surface, at least a portion of each of the first interior adhesive surface and the second interior adhesive surface being exposed to the enclosed area so as to form the interior coating, such that the enclosed area is entirely surrounded by the interior coating for the adherence of particles or dust present within the enclosed area resulting from mechanical damage of one or more of the plurality of converter elements.

* * * * *